United States Patent [19]

Kitano et al.

[11] Patent Number: 4,877,548

[45] Date of Patent: Oct. 31, 1989

[54] LIQUID CRYSTAL COMPOSITION

[75] Inventors: Kisei Kitano, Chiba; Makoto Ushioda; Manabu Uchida, both of Ichihara; Toshiharu Suzuki, Ichihara, all of Japan

[73] Assignee: Chisso Corporation, Japan

[21] Appl. No.: 290,701

[22] Filed: Dec. 27, 1988

[30] Foreign Application Priority Data

Dec. 28, 1987 [JP] Japan ................................ 62-335984

Jun. 3, 1988 [JP] Japan ................................ 63-136820

[51] Int. Cl.[4] ........................ G02F 1/13; C09K 19/30; C09K 19/12; C07C 21/24

[52] U.S. Cl. ............................ 252/299.63; 252/299.5; 252/299.6; 252/299.66; 350/350 R; 568/609; 568/610; 568/611; 568/612; 568/606; 568/642; 568/643; 568/645; 568/647; 568/660; 568/661; 568/664; 570/128; 570/129; 570/130

[58] Field of Search ............ 252/299.5, 299.63, 299.6, 252/299.66; 568/609, 610, 611, 612, 606, 642, 643, 645, 647, 660, 661, 664; 350/350 R; 570/128, 129, 130

[56] References Cited

U.S. PATENT DOCUMENTS

| | | | |
|---|---|---|---|
| 4,363,767 | 12/1982 | Demus et al. | 252/299.63 |
| 4,460,770 | 7/1984 | Petrzilka et al. | 252/299.6 |
| 4,528,114 | 7/1985 | Petrzilka | 252/299.63 |
| 4,565,425 | 1/1986 | Petrzilka et al. | 252/299.6 |
| 4,676,604 | 6/1987 | Petrzilka | 252/299.63 |
| 4,709,030 | 11/1987 | Petrzilka et al. | 252/299.6 |
| 4,723,005 | 2/1988 | Huynm-Ba et al. | 252/299.63 |
| 4,770,503 | 9/1988 | Buchecker et al. | 250/299.63 |

FOREIGN PATENT DOCUMENTS

| | | | |
|---|---|---|---|
| 3601452 | 7/1987 | Fed. Rep. of Germany | 252/299.6 |
| 87/01701 | 3/1987 | PCT Int'l Appl. | 252/299.63 |

*Primary Examiner*—Teddy S. Gron

*Attorney, Agent, or Firm*—Leydig, Voit & Mayer

[57] ABSTRACT

A liquid crystalline compound and a liquid crystal composition containing the compound usable for liquid crystal display devices are provided, which liquid crystalline compound is expressed by the formula $$R^1{-}A^1{-}B^1{-}A^2{-}(B^2{-}A^3)_n{-}(CH_2)_m{-}CH{=}CF_2$$

wherein $R^1$ is H or 1-20C alkyl or alkenyl wherein one $-CH_2-$group or two $-CH_2-$ groups not adjacent to each other may be substituted by —O—; the position and number of the double bond may be optionally chosen; $A^1$, $A^2$ and $A^3$ each are

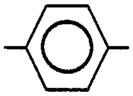 or 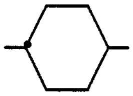

and the H of the

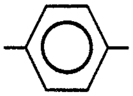

may be substituted by F, Cl or methyl; $B^1$ and $B^2$ each are $-CH_2CH_2-$, $-CH_2O-$, $-OCH_2-$ or a single bond; n is 0 or 1; and m is 0-20.

16 Claims, No Drawings

LIQUID CRYSTAL COMPOSITION

BACKGROUND OF THE INVENTION

This invention relates to a novel liquid crystal compound and a liquid crystal composition containing the compound.

Liquid crystal substances and compositions thereof have been used for various display devices, utilizing the dielectric anisotropy (hereinafter abbreviated to $\Delta\epsilon$) and the optical anisotropy (hereinafter abbreviated to $\Delta n$) in the liquid crystal phases thereof.

Liquid crystal display modes include various ones such as electric ally controlled birefringence type (ECB type), twisted nematic type (TN type), super twisted birefringence type (SBE type), dynamic scattering type (DS type), guest-host type, etc., which correspond to various electro-optical effects applied.

Liquid crystal materials used for display devices should provide together various specific features such as a broad mesomorphic range, a low viscosity, a large positive $\Delta\epsilon$ value or a negative $\Delta\epsilon$ value, no notable change in various specific features (particularly, threshould voltage) over a broad liquid crystal phase temperature range, etc., depending on the display modes thereof or on various specific features required for the display elements thereof.

At present, however, there is no single compound which is practically usable, in the aspects of liquid crystal phase temperature range, driving voltage and response performance. Thus, for practical use, mixtures of several kinds of liquid crystal compounds or mixtures of several kinds of liquid crystal compounds with compounds having latent liquid crystal properties or non-liquid crystal compounds have been used.

SUMMARY OF THE INVENTION

The object of the present invention is to provide a liquid crystalline compound and a liquid crystal composition usable for liquid crystal display devices. The liquid crystalline compound referred to herein means both compounds of those exhibiting liquid crystal phases and those which usually exhibit no liquid crystal phase, but when dissolved in other liquid crystal compounds, effectively function in a certain aspect of liquid crystal behavior.

The present invention in a first aspect resides in (1) a compound expressed by the formula $$R^1—A^1—B^1—A^2—B^2—A^3)_n(CH_2)_mCH{=}CF_2 \quad (I)$$

wherein $R^1$ represents hydrogen atom or an alkyl group or an alkenyl group each of 1 to 20 carbon atoms wherein one $—CH_2—$ group or two $—CH_2—$ groups not adjacent to each other may be substituted by —O— group; the position and number of double bond in the alkeny group may be optionally chosen; $A^1$, $A^2$ and $A^3$ each independently represent

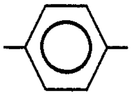

or

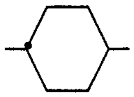

and the hydrogen atoms of this

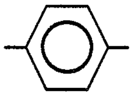

may be substituted by fluorine, chlorine or methyl; $B^1$ and $B^2$ each independently represent $—CH_2CH_2—$, $—CH_2O—$, $—OCH_2—$ or a single bond; n represents an integer of 0 or 1; and m represents an integer of 0 to 20.

The present invention in a second aspect resides in (2) a liquid crystal composition comprising two components at least one of which is a compound expressed by the above formula (I).

DETAILED DESCRIPTION OF PREFERRED EMBODIMENTS

Among the compounds of the present invention expressed by the formula (I) wherein n=0, examples of preferred compounds are those expressed by the following formulas:

(1)

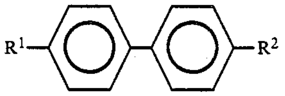

(2)

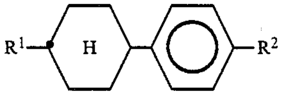

(3)

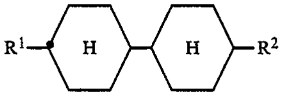

(4)

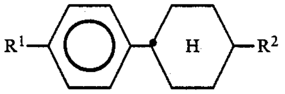

(5)

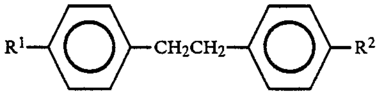

(6)

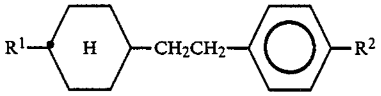

(7)

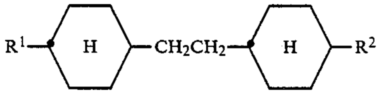

(8)

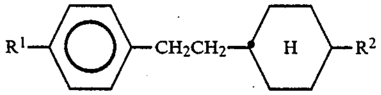

-continued

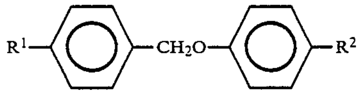

(9)

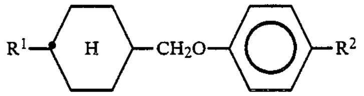

(10)

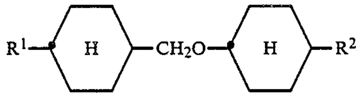

(11)

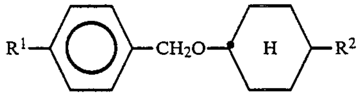

(12)

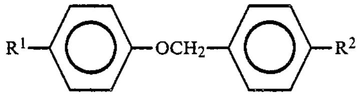

(13)

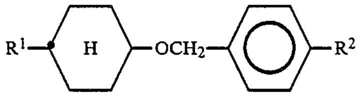

(14)

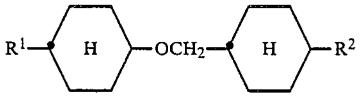

(15)

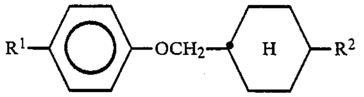

(16)

In these formulas, $R^1$ is as defined above, $R^2$ represents $-(CH_2)_m CH{=}CF_2$ wherein m represents an integer of 0 to 20 and the phenylene ring may be substituted by

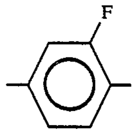

or

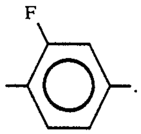

.

Among the compounds of the present invention expressed by the above formulas and having two sixmembered rings, those wherein $R^1$ represents a linear alkyl or alkoxy group each of 1 to 12 carbon atoms are preferred.

Further, compounds wherein m in $R^2$ represents 0 are abundant in nematic properties and include a number of compounds exhibiting nematic phase with a broad temperature range including room temperature.

Further, compounds wherein m in $R^2$ represents 1 to 10 are also preferred.

These two-ring compounds have a very low viscosity and a superior compatibility with other existing liquid crystals. Thus, even when liquid crystal compounds which have so far not been practical due to their low compatibility are dissolved in the above compounds, nematic mixtures can be formed; hence the above compounds have an advantage of being able to broaden the range of practical liquid crystal materials.

Among the compound of the formula (I) wherein n=1, examples of preferred compounds are those expressed by the following formulas:

(17)

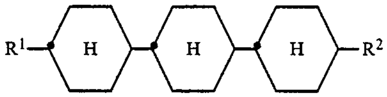

(18)

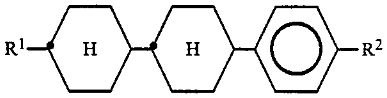

(19)

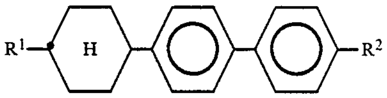

(20)

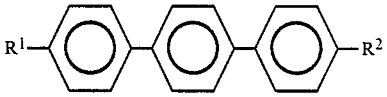

(21)

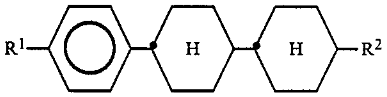

(22)

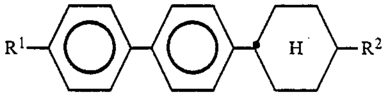

(23)

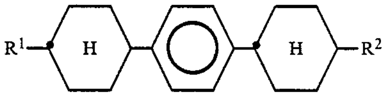

(24)

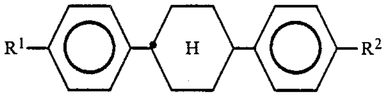

(25)

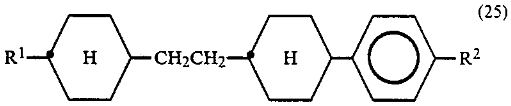

In these formulas, $R^1$ and $R^2$ are as defined above and the phenylene ring may be substituted by

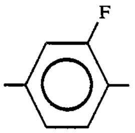

or

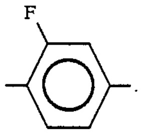

.

Among these compounds, those having m in $R^2$ of the formulas of 0–10 are particularly preferred.

The compound of the present invention may be prepared for example according to the following route:

$$R^1—A^1—B^1—A^2—(B^2—A^3)_n—(CH_2)_m—CHO \qquad (II)$$

$PPh_3$
$ClF_2CCOONa$
Diethylene glycol dimethyl ether $$R^1—A^1—B^1—A^2—(B^2—A^3)_n—(CH_2)_m—CH{=}CF_2 \qquad (I)$$

wherein $R^1$, $A^1$, $A^2$, $A^3$, $B^1$, $B^2$, n and m are as defined above and Ph represents phenyl.

Namely, an aldehyde derivative expressed by the formula (II) is reacted with triphenylphosphine and sodium chlorodifluoroacetate in a solvent of diethylene glycol dimethyl ether under reflux. This reaction is known as Wittig reaction wherein carbon-carbon double bond is formed (e.g. see Org. Synth. col. Vol. V, 390 (1973). By subjecting the reaction product to separation and purification operations such as vacuum distillation, chromatography, recrystallization, etc., it is possible to obtain a 2,2-difluoroethene derivative of the formula (I).

The aldehyde derivative of the formula (II) as the starting raw material may be prepared for example through the following route:

$$R^1—A^1—B^1—A^2—(B^2—A^3)_n—CN \qquad (IV)$$

$(i\text{-}Bu)_2AlH$
Toluene $$R^1—A^1—B^1—A^2—(B^2—A^3)_n—CHO \qquad (V)$$

$Ph_3P^+CH_2OCH_3Cl^-$
Base $$R^1—A^1—B^1—A^2—(B^2—A^3)_n—CH{=}CHOCH_3 \qquad (VI)$$

$H^+$ $$R^1—A^1—B^1—A^2—(B^2—A^3)_n—CH_2CHO \qquad (VII)$$

wherein $R^1$, $A^1$, $B^1$, $A^2$, $B^2$, $A^3$ and n are as defined above, and i-Bu and Ph represent isobutyl and phenyl, respectively.

Namely, a substituted-benzonitrile or a substituted-cyclohexanecarbonitrile of the formula (IV) is reacted with diisobutylaluminum hydride in dried toluene solvent at a low temperature, followed by treating the reaction mixture with methanol, water and further, hydrochloric acid, extracting the product with toluene, neutralizing the extract solution, washing with water, drying and subjecting the resulting product to general separation and purification steps such as vacuum distillation, chromatography, recrystallization, etc. to obtain a substituted-benzaldehyde or a substituted-cyclohexanecarbaldehyde of the formula (V). These compounds are aldehyde derivatives (II) in the case of $m=0$.

The compound of the formula (IV) as the starting raw material includes a number of compounds which themselves have been used as liquid crystal materials, and other compounds may also be easily prepared by combining preparation of liquid crystal compounds or known reactions therewith.

Further, besides the above preparation using the nitrile derivative of the formula (IV) as the starting raw material, other preparations may also be employed wherein a substituted-benzoic acid, a substituted-cyclohexanecarboxylic acid, a substituted-benzyl alcohol, a substituted-cyclohexylmethanol or the like is reduced or oxidized to obtain the aldehyde compound of the formula (V).

Further, a methoxyvinyl derivative of formula (VI) is obtained according to a Wittig reaction wherein the aldehyde derivative (V) is reacted with methoxymethyltriphenylphosphonium chloride and a base such as potassium t-butoxide, sodium methylate, phenyllithium, n-butyllithium, etc. When this compound (VI) is heated under a acidic condition (for example, heated together with hydrochloric acid in tetrahydrofuran solvent), it is possible to obtain an aldehyde derivative (VII) having one more methylene group than the original aldehyde derivative (V). By repeating the Wittig reaction and the acid treatment reaction using the aldehyde derivative (V) as starting raw material m times, it is possible to obtain the aldehyde derivative (II) having m of one or more.

The compound of the formula (I) of the present invention is a liquid crystalline compound having a relatively low viscosity and also a compound suitable for preparing a liquid crystal display device having a high response rate.

The compound of the present invention is stable to heat, light, electricity, moisture, etc., required for liquid crystal display materials. Further, the compound of the present invention has a superior compatibility with other liquid crystalline compounds; hence when the compound is mixed with these compounds or mixtures thereof, it is possible to obtain liquid crystal materials suitable to various use applications.

As liquid crystal components used as components of the liquid crystal composition of the present invention besides the compound of the formula (I), for example, liquid crystal compounds expressed by the following formulas (i) to (xxiii) are preferred:

(i)

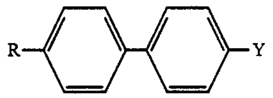

(ii)

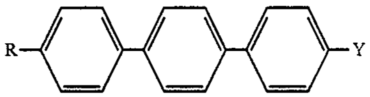

(iii)

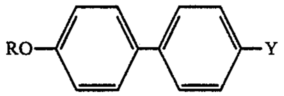

(iv)

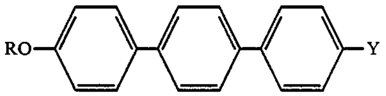

(v)

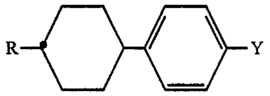

(vi)

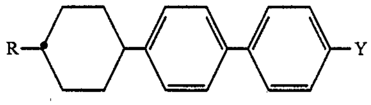

-continued
(vii)
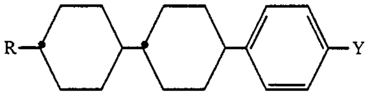
(viii)
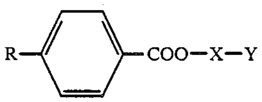
(ix)
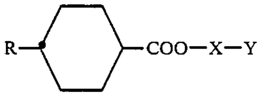
(x)
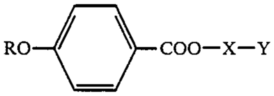
(xi)
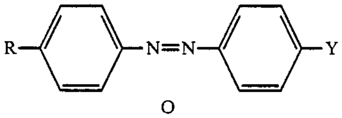
(xii)
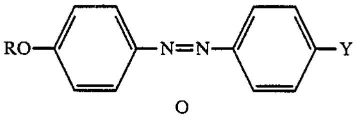
(xiii)
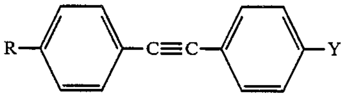
(xiv)
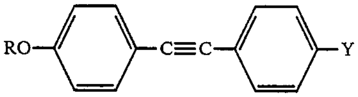
(xv)
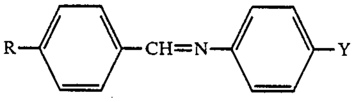
(xvi)
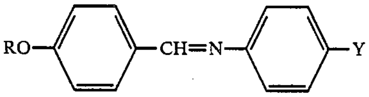
(xvii)
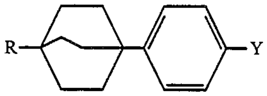
(xviii)
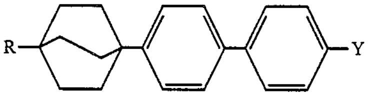
(xix)
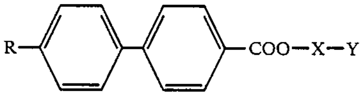
-continued
(xx)
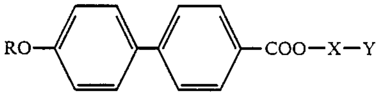
(xxi)
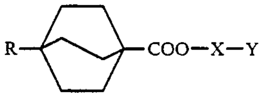
(xxii)
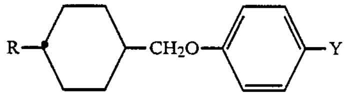
(xxiii)
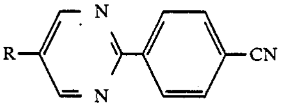
(xxiv)
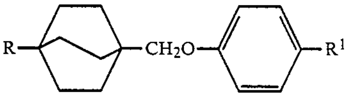
(xxv)
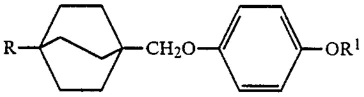
(xxvi)
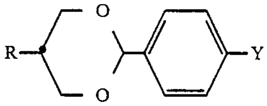
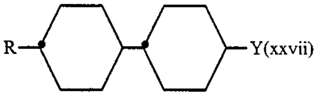
(xxvii)
(xxviii)
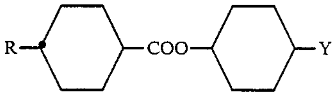
(xxix)
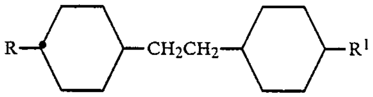
(xxx)
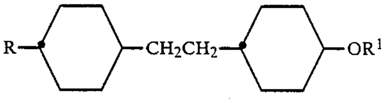
(xxxi)
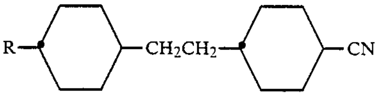
(xxxii)
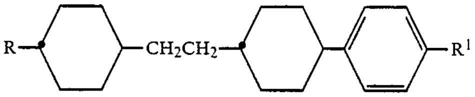

-continued (xxxiii)

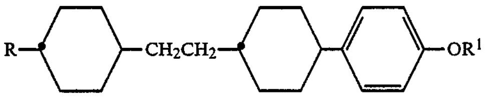

In the formulas (i)-(xxxiii), X represents

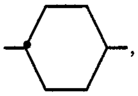, 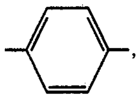, 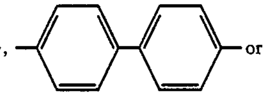 or

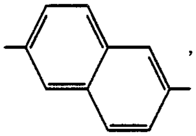,

Y represents —CN, 9 halogen atom, $R^1$ or $OR^1$, R and $R^1$ each represent an alkyl group and the hydrogen atom of

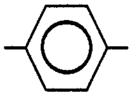

may be substituted by halogen atom.

In the present invention, with these liquid crystal compounds or liquid crystal mixtures is mixed the compound of the formula (I) in 1 to 30% by weight, preferably 5 to 20% by weight.

If the content of the compound of the formula (I) wherein m=1-20 and n=0 exceeds 30% by weight, the clearing point of the resulting composition lowers notably; hence, such excess content is undesirable. Further, if the content of the compound of the formula (I) wherein m=1-20 and n=1 exceeds 30% by weight, the viscosity of the resulting composition often becomes high; hence, such excess content is also undesirable.

The two-ring compounds of the above-mentioned formulas (1)-(16) have specific features wherein they have a very low viscosity and a superior compatibility with other existing liquid crystals and even when they are added to nematic liquid crystal compositions, the nematic-isotropic liquid phase transition points are not lowered noticeably. Particularly the compound of the formula (3) has a very small Δn; hence the compound is useful for preparing a liquid crystal composition having a small Δn.

Further the three-ring liquid crystalline compounds of the above-mentioned formulas (17)-(25) include a number of compounds having a higher clearing point than those of the two-ring compounds. These compounds have a relatively low viscosity for the three-ring liquid crystal compounds.

The present invention will be described in more detail by way of Examples, but it should not be construed to be limited thereto. In the examples, crystallinesmectic phase transition point, crystalline-nematic phase transition point, smectic-smectic phase transition point, smectic-nematic phase transition point, smectic-isotropic liquid phase transition point and nematic-isotropic liquid phase transition point will be abbreviated to CS point, CN point, SS point, SN point, SI point and NI point, respectively.

EXAMPLE 1

(i) Preparation of 4-(trans-4-propylcyclohexyl)-benzaldehyde

A mixture of trans-4-propyl-(4-cyanophenyl)cyclohexane (100 g, 0.44 mol) and dried toluene (200 ml) was purged with nitrogen gas at 0° C. with stirring, followed by gradually adding a 25 wt. % toluene solution (300g) of diisobutylaluminum hydride in a nitrogen gas current at a reaction temperature of 5° C. or lower, with stirring, gradually raising the reaction temperature up to 20° C. over 3 hours, agitating the resulting mixture at 20° C. for 10 hours in a nitrogen gas current, cooling the reaction mixture down to 0° C., dropwise adding methanol (200 ml), water (200 ml) and further 6N-hydrochloric acid (500 ml) with stirring, adding toluene (300 ml) to the reaction mixture to extract the reaction product, washing the toluene solution five times with a saturated aqueous solution (200 ml) of sodium hydrogen carbonate and further washing with water till the washing liquid became neutral, drying the resulting toluene solution over anhydrous sodium sulfate, filtering off the drying agent, distilling off toluene and distilling the residue under reduced pressure (160° C., 2 mmHg) to obtain the objective product (89 g, 0.39 mol).

(ii) Preparation of trans-4-propyl-[4-(2,2-difluoro-1-ethenyl)phenyl]cyclohexane While 4-(trans-4-n-propylcyclohexyl)benzaldehyde (25 g, 0.11 mol), triphenylphosphine (31 g, 0.12 mol) and diethylene glycol dimethyl ether (25 ml) were heated at 160° C. in nitrogen gas current with stirring, a solution of sodium chlorodifluoroacetate (25 g, 0.16 mol) in diethylene glycol dimethyl ether (70 ml) at 70° C. was dropwise added to the above solution over 2 hours, followed by cooling the resulting solution, filtering it by suction, concentrating the filtrate under reduced pressure, distilling the concentrate under reduced pressure (150° C., 3 mmHg), dissolving the distillate in toluene (100 ml), washing the toluene solution three times with 6N-hydrochloric acid (100 ml) and further with water till the washing water became neutral, drying the toluene solution with anhydrous sodium sulfate, separating the drying agent, distilling off toluene, recrystallizing the residue from a mixed solvent of heptane with ethanol (1:5), dissolving the resulting crystals in heptane, purifying the solution according to silica gel column chromatography, again distilling the resulting solution under reduced pressure, three times recrystallizing the residue from a mixed solvent of heptane with ethanol (1:5) and finally drying the resulting crystals to obtain the objective product (10 g, 0.04 mol).

The values of the physical properties of this compound were as follows:

| | |
|---|---|
| CN point | 6.8-7.8° C. |
| NI point | 48.0° C. |
| Viscosity at 20° C. | 5.0 cP |
| Δn at 25° C. | 0.10 ($n_e$ = 1.482, $n_o$ = 1.587) |
| Δε at 25° C. | 1.93 ($\epsilon_{\|\|}$ = 5.08, $\epsilon_{\perp}$ = 3.15) |

Similarly, the following trans-4-alkyl[4-(2,2-difluoro-1-ethenyl) phenyl]cyclohexanes can be prepared using the corresponding trans-4-substituted-(4-cyanophenyl)-cyclohexanes as raw materials:

trans-4-methyl-[4-(2,2-difluoro-1-ethenyl)phenyl]-cyclohexane trans-4-ethyl[4-(2,2-difluoro-1-ethenyl)phenyl]-cyclohexane CN point 0.0°-1.0° C., NI point 12.9°-13.0° C.

trans-4-butyl-[4-(2,2-difluoro-1-ethenyl)phenyl]-cyclohexane trans-4-pentyl-[4-(2,2-difluoro-1-ethenyl)phenyl]-cyclohexane CN point 9.2°-9.8° C., NI point 60.2° C.

trans-4-hexyl-[4-(2,2-diluoro-1-ethenyl)phenyl]-cyclohexane trans-4-heptyl-[4-(2,2-difluoro-1-ethenyl)phenyl]-cyclohexane trans-4-octyl-[4-(2,2-diluoro-1-ethenyl)phenyl]-cyclohexane trans-4-nonyl-[4-(2,2-difluoro-1-ethenyl)phenyl]-cyclohexane trans-4-decyl-[4-(2,2-diluoro-1-ethenyl)phenyl]-cyclohexane trans-4-undecyl-[4-(2,2-difluoro-1-ethenyl)phenyl]-cyclohexane trans-4-dodecyl-[4-(2,2-difluoro-1-ethenyl)phenyl]-cyclohexane trans-4-methoxymethyl-[4-(2,2-difluoro-1-ethenyl)-phenyl]-cyclohexane trans-4-methoxy-[4-(2,2-difluoro-1-ethenyl)phenyl]-cyclohexane trans-4-ethoxy-[4-(2,2-difluoro-1-ethenyl)phenyl]-cyclohexane trans-4-propoxy-[4-(2,2-difluoro-1-ethenyl)phenyl]-cyclohexane trans-4-butoxy-[4-(2,2-difluoro-1-ethenyl)phenyl]-cyclohexane trans-4-pentyloxy-[4-(2,2-difluoro-1-ethenyl)phenyl]-cyclohexane trans-4-hexyloxy-[4-(2,2-difluoro-1-ethenyl)phenyl]-cyclohexane trans-4-heptyloxy-[4-(2,2-difluoro-1-ethenyl)phenyl]-cyclohexane trans-4-octyloxy-[4-(2,2-difluoro-1-ethenyl)phenyl]-cyclohexane trans-4-nonyloxy-[4-(2,2-difluoro-1-ethenyl)phenyl]-cyclohexane trans-4-decyloxy-[4-(2,2-difluoro-1-ethenyl)phenyl]-cyclohexane trans-4-undecyloxy-[4-(2,2-difluoro-1-ethenyl)-phenyl]-cyclohexane trans-4-dodecyloxy-[4-(2,2-difluoro-1-ethenyl)-phenyl]-cyclohexane

EXAMPLE 2

Trans-4-pentyl-[3-fluoro-4-(2,2-difluoro-1-ethenyl)-phenyl]cyclohexane was prepared in the same manner as in Example 1, using trans-4-pentyl-(3-fluoro-4-cyano-phenyl)-cyclohexane as starting raw material. This product exhibited liquid crystal phases and CN point was −0.2° to 0.0° C. and NI point was 30.8° C. Further, this compound had a viscosity of 7.1 cP at 20° C. and a $\Delta\epsilon$ of 2.2 ($\epsilon_{//}=6.00$, $\epsilon_{\perp}=3.80$) and a $\Delta n$ of 0.078 ($n_e=1.555$, $n_0=1.477$) as measured at 25° C.

Similarly the following compounds can be prepared:

trans-4-methyl-[3-fluoro-4-(2,2-difluoro-1-ethenyl)-phenyl]cyclohexane trans-4-ethyl-[3-fluoro-4-(2,2-difluoro-1-ethenyl)-phenyl]cyclohexane trans-4-propyl-[3-fluoro-4-(2,2-difluoro-1-ethenyl)-phenyl]cyclohexane trans-4-butyl-[3-fluoro-4-(2,2-difluoro-1-ethenyl)-phenyl]cyclohexane trans-4-hexyl-[3-fluoro-4-(2,2-difluoro-1-ethenyl)-phenyl]cyclohexane trans-4-heptyl-[3-fluoro-4-(2,2-difluoro-1-ethenyl)-phenyl]cyclohexane trans-4-octyl-[3-fluoro-4-(2,2-difluoro-1-ethenyl)-phenyl]cyclohexane trans-4-nonyl-[3-fluoro-4-(2,2-difluoro-1-ethenyl)-phenyl]cyclohexane trans-4-decyl-[3-fluoro-4-(2,2-difluoro-1-ethenyl)-phenyl]cyclohexane trans-4-undecyl-[3-fluoro-4-(2,2-difluoro-1-ethenyl)-phenyl]cyclohexane trans-4-dodecyl-[3-fluoro-4-(2,2-difluoro-1-ethenyl)-phenyl]cyclohexane trans-4-methoxymethyl-[3-fluoro-4-(2,2-difluoro-1-ethenyl)phenyl]cyclohexane trans-4-methoxy-[3-fluoro-4-(2,2-difluoro-1-ethenyl)-phenyl]cyclohexane trans-4-ethoxy-[3-fluoro-4-(2,2-difluoro-1-ethenyl)-phenyl]cyclohexane trans-4-propoxy-[3-fluoro-4-(2,2-difluoro-1-ethenyl)-phenyl]cyclohexane trans-4-butoxy-[3-fluoro-4-(2,2-difluoro-1-ethenyl)-phenyl]cyclohexane trans-4-pentyloxy-[3-fluoro-4-(2,2-difluoro-1-ethenyl)phenyl]cyclohexane trans-4-hexyloxy-[3-fluoro-4-(2,2-difluoro-1-ethenyl)-phenyl]cyclohexane trans-4-heptyloxy-[3-fluoro-4-(2,2-difluoro-1-ethenyl)phenyl]cyclohexane trans-4-octyloxy-[3-fluoro-4-(2,2-difluoro-1-ethenyl)-phenyl]cyclohexane trans-4-nonyloxy-[3-fluoro-4-(2,2-difluoro-1-ethenyl)phenyl]cyclohexane trans-4-decyloxy-[3-fluoro-4-(2,2-difluoro-1-ethenyl)-phenyl]cyclohexane trans-4-undecyloxy-[3-fluoro-4-(2,2-difluoro-1-ethenyl)phenyl]cyclohexane trans-4-dodecyloxy-[3-fluoro-4-(2,2-difluoro-1-ethenyl)phenyl]cyclohexane

EXAMPLE 3

Trans-4-(trans-4-propylcyclohexyl)-1-[4-(2,2-difluoro-1-ethenyl)phenyl]cyclohexane was prepared in the same manner as in Example 1, using trans-4-(trans-4-propylcyclohexyl)cyclohexylbenzonitrile as starting raw material.

This product exhibited the following liquid crystal phases: CS point 51.0° C., SN point 88.6° C. and NI point 233° C.

Similarly the following compounds are prepared:

trans-4-(trans-4-methylcyclohexyl)-1-[4-(2,2-difluoro-1-ethenyl)phenyl]cyclohexane trans-4-(trans-4-ethylcyclohexyl)-1-[4-(2,2-difluoro-1-ethenyl)phenyl]cyclohexane trans-4-(trans-4-butylcyclohexyl)-1-[4-(2,2-difluoro-1-ethenyl)phenyl]cyclohexane trans-4-(trans-4-pentylcyclohexyl)-1-[4-(2,2-difluoro-1-ethenyl)phenyl]cyclohexane trans-4-(trans-4-hexylcyclohexyl)-1-[4-(2,2-difluoro-1-ethenyl)phenyl]cyclohexane trans-4-(trans-4-heptylcyclohexyl)-1-[4-(2,2-difluoro-1-ethenyl)phenyl]cyclohexane trans-4-(trans-4-octylcyclohexyl)-1-[4-(2,2-difluoro-1-ethenyl)phenyl]cyclohexane trans-4-(trans-4-nonylcyclohexyl)-1-[4-(2,2-difluoro-1-ethenyl)phenyl]cyclohexane trans-4-(trans-4-decylcyclohexyl)-1-[4-(2,2-difluoro-1-ethenyl)phenyl]cyclohexane trans-4-(trans-4-methoxymethylcyclohexyl)-1-[4-(2,2-difluoro-1-ethenyl)phenyl]cyclohexane trans-4-(trans-4-methoxycyclohexyl)-1-[4-(2,2-difluoro-1-ethenyl)phenyl]cyclohexane trans-4-(trans-4-ethoxycyclohexyl)-1-[4-(2,2-difluoro-1-ethenyl)phenyl]cyclohexane trans-4-(trans-4-propoxycyclohexyl)-1-[4-(2,2-difluoro-1-ethenyl)phenyl]cyclohexane trans-4-(trans-4-butoxycyclohexyl)-1-[4-(2,2-difluoro-1-ethenyl)phenyl]cyclohexane trans-4-(trans-4-pentyloxycyclohexyl)-1-[4-(2,2-difluoro-1-ethenyl)phenyl]cyclohexane trans-4-(trans-4-hexyloxycyclohexyl)-1-[4-(2,2-difluoro-1-ethenyl)phenyl]cyclohexane trans-4-(trans-4-heptyloxycyclohexyl)-1-[4-(2,2-difluoro-1-ethenyl)phenyl]cyclohexane trans-4-(trans-4-octyloxycyclohexyl)-1-[4-(2,2-difluoro-1-ethenyl)phenyl]cyclohexane trans-4-(trans-4-nonyloxycyclohexyl)-1-[4-(2,2-difluoro-1-ethenyl)phenyl]cyclohexane trans-4-(trans-4-decyloxycyclohexyl)-1-[4-(2,2-difluoro-1-ethenyl)phenyl]cyclohexane trans-4-(trans-4-undecyloxycyclohexyl)-1-[4-(2,2-difluoro-1-ethenyl)phenyl]cyclohexane trans-4-(trans-4-dodecyloxycyclohexyl)-1-[4-(2,2-difluoro-1-ethenyl)phenyl]cyclohexane trans-4-[trans-4-(2,2-difluoro-1-ethenyl)cyclohexyl]-1-(4-methylphenyl)cyclohexane trans-4-[trans-4-(2,2-difluoro-1-ethenyl)cyclohexyl]-1-(4-ethylphenyl)cyclohexane trans-4-[trans-4-(2,2-difluoro-1-ethenyl)cyclohexyl]-1-(4-propylphenyl)cyclohexane trans-4-[trans-4-(2,2-difluoro-1-ethenyl)cyclohexyl]-1-(4-butylphenyl)cyclohexane trans-4-[trans-4-(2,2-difluoro-1-ethenyl)cyclohexyl]-1-(4-pentylphenyl)cyclohexane trans-4-[trans-4-(2,2-difluoro-1-ethenyl)cyclohexyl]-1-(4-hexylphenyl)cyclohexane trans-4-[trans-4-(2,2-difluoro-1-ethenyl)cyclohexyl]-1-(4-heptylphenyl)cyclohexane trans-4-[trans-4-(2,2-difluoro-1-ethenyl)cyclohexyl]-1-(4-octylphenyl)cyclohexane 4-[trans-4(2,2-difluoro-1-ethenyl)cyclohexyl]-4'-methylbiphenyl 4-[trans-4(2,2-difluoro-1-ethenyl)cyclohexyl]-4'-ethylbiphenyl 4-[trans-4(2,2-difluoro-1-ethenyl)cyclohexyl]-4'-propylbiphenyl 4-[trans-4(2,2-difluoro-1-ethenyl)cyclohexyl]-4'-butylbiphenyl 4-[trans-4(2,2-difluoro-1-ethenyl)cyclohexyl]-4'-pentylbiphenyl 4-[trans-4(2,2-difluoro-1-ethenyl)cyclohexyl]-4'-hexylbiphenyl 4-[trans-4(2,2-difluoro-1-ethenyl)cyclohexyl]-4'-heptylbiphenyl 4-[trans-4(2,2-difluoro-1-ethenyl)cyclohexyl]-4'-octylbiphenyl

EXAMPLE 4

Example 1 was repeated except that the starting raw material was replaced by trans-4-(4-pentylphenyl)cyclohexanecarbonitrile to obtain trans-4-(4-pentylphenyl)-1(2,2-difluoro-1-ethenyl)cyclohexane.

The melting point of this product was −17.0° to −16.0° C.

Similarly the following compounds can be prepared:

trans-4-(p-tolyl)-1-(2,2-difluoro-1-ethenyl)cyclohexane trans-4-(4-ethylphenyl)-1-(2,2-difluoro-1-ethenyl)cyclohexane trans-4-(4-propylphenyl)-1-(2,2-difluoro-1-ethenyl)cyclohexane m.p −11.9° to −11.6° C.

trans-4-(4-butylphenyl)-1-(2,2-difluoro-1-ethenyl)cyclohexane trans-4-(4-hexylphenyl)-1-(2,2-difluoro-1-ethenyl)cyclohexane trans-4-(4-heptylphenyl)-1-(2,2-difluoro-1-ethenyl)cyclohexane trans-4-(4-octylphenyl)-1-(2,2-difluoro-1-ethenyl)cyclohexane trans-4-(4-nonylphenyl)-1-(2,2-difluoro-1-ethenyl)cyclohexane trans-4-(4-decylphenyl)-1-(2,2-difluoro-1-ethenyl)cyclohexane trans-4-(4-undecylphenyl)-1-(2,2-difluoro-1-ethenyl)cyclohexane trans-4-(4-dodecylphenyl)-1-(2,2-difluoro-1-ethenyl)cyclohexane trans-4-(4-methoxyphenyl)-1-(2,2-difluoro-1-ethenyl)cyclohexane trans-4-(4-ethoxyphenyl)-1-(2,2-difluoro-1-ethenyl)cyclohexane trans-4-(4-propoxyphenyl)-1-(2,2-difluoro-1-ethenyl)cyclohexane trans-4-(4-butoxyphenyl)-1-(2,2-difluoro-1-ethenyl)cyclohexane trans-4-(4-pentyloxphenyl)-1-(2,2-difluoro-1-ethenyl)cyclohexane trans-4-(4-hexyloxyphenyl)-1-(2,2-difluoro-1-ethenyl)cyclohexane trans-4-(4-heptyloxyphenyl)-1-(2,2-difluoro-1-ethenyl)cyclohexane trans-4-(4-oxtyloxyphenyl)-1-(2,2-difluoro-1-ethenyl)cyclohexane trans-4-(4-nonyloxyphenyl)-1-(2,2-difluoro-1-ethenyl)cyclohexane trans-4-(4-decyloxyphenyl)-1-(2,2-difluoro-1-ethenyl)cyclohexane trans-4-(4-undecyloxyphenyl)-1-(2,2-difluoro-1-ethenyl)cyclohexane trans-4-(4-dodecyloxyphenyl)-1-(2,2-difluoro-1-ethenyl)cyclohexane trans-4-(4-methoxymethylphenyl)-1-(2,2-difluoro-1-ethenyl)cyclohexane.

EXAMPLE 5

Example 1 was repeated except that the starting raw material was replaced by 4-hexyl-4'-cyanobiphenyl to obtain 4-hexyl-4'-(2,2-difluoro-1-ethenyl)biphenyl.

The physical properties were as follows:

CS point 59° C. and SI point 95.8° C.

Similarly the following compounds are prepared:

4-methyl-4'-(2,2-difluoro-1-ethenyl)biphenyl
4-ethyl-4'-(2,2-difluoro-1-ethenyl)biphenyl
4-propyl-4'-(2,2-difluoro-1-ethenyl)biphenyl
4-butyl-4'-(2,2-difluoro-1-ethenyl)biphenyl
4-pentyl-4'-(2,2-difluoro-1-ethenyl)biphenyl
4-heptyl-4'-(2,2-difluoro-1-ethenyl)biphenyl
4-octyl-4'-(2,2-difluoro-1-ethenyl)biphenyl
4-nonyl-4'-(2,2-difluoro-1-ethenyl)biphenyl
4-decyl-4'-(2,2-difluoro-1-ethenyl)biphenyl
4-undecyl-4'-(2,2-difluoro-1-ethenyl)biphenyl
4-dodecyl-4'-(2,2-difluoro-1-ethenyl)biphenyl
4-methoxy-4'-(2,2-difluoro-1-ethenyl)biphenyl
4-ethoxy-4'-(2,2-difluoro-1-ethenyl)biphenyl
4-propoxy-4'-(2,2-difluoro-1-ethenyl)biphenyl 4-butoxy-4'-(2,2-difluoro-1-ethenyl)biphenyl
4-pentyloxy-4'-(2,2-difluoro-1-ethenyl)biphenyl
4-hexyloxy-4'-(2,2-difluoro-1-ethenyl)biphenyl
4-heptyloxy-4'-(2,2-difluoro-1-ethenyl)biphenyl
4-octyloxy-4'-(2,2-difluoro-1-ethenyl)biphenyl
4-nonyloxy-4'-(2,2-difluoro-1-ethenyl)biphenyl
4-decyloxy-4'-(2,2-difluoro-1-ethenyl)biphenyl
4-undecyloxy-4'-(2,2-difluoro-1-ethenyl)biphenyl
4-dodecyloxy-4'-(2,2-difluoro-1-ethenyl)biphenyl
4-methoxymethyl-4'-(2,2-difluoro-1-ethenyl)biphenyl
4-(trans-4-methylcyclohexyl)-4'-(2,2-difluoro-1-ethenyl)biphenyl
4-(trans-4-ethylcyclohexyl)-4'-(2,2-difluoro-1-ethenyl)biphenyl
4-(trans-4-propylcyclohexyl)-4'-(2,2-difluoro-1-ethenyl)biphenyl
4-(trans-4-butylcyclohexyl)-4'-(2,2-difluoro-1-ethenyl)biphenyl
4-(trans-4-pentylcyclohexyl)-4'-(2,2-difluoro-1-ethenyl)biphenyl
CS point 56.7°-57.7° C., SN point 184° C., NI point 232° C.
4-(trans-4-hexylcyclohexyl)-4'-(2,2-difluoro-1-ethenyl)biphenyl
4-(trans-4-heptylcyclohexyl)-4'-(2,2-difluoro-1-ethenyl)biphenyl
4-(trans-4-octylcyclohexyl)-4'-(2,2-difluoro-1-ethenyl)biphenyl
4-(trans-4-nonylcyclohexyl)-4'-(2,2-difluoro-1-ethenyl)biphenyl
4-(trans-4-decylcyclohexyl)-4'-(2,2-difluoro-1-ethenyl)biphenyl
4-(trans-4-methoxymethylcyclohexyl)-4'-(2,2-difluoro-1-ethenyl)biphenyl.

EXAMPLE 6

Example 1 was repeated except that the starting raw material was replaced by trans-4-(trans-4-propylcyclohexyl)cyclohexanecarbonitrile to prepare trans4-(trans-4-propylcyclohexyl)-1-(2,2-difluoro-1-ethenyl)-cyclohexane.

This product exhibited the following liquid crystal phases:

CS point −0.7° to +0.5° C., SN point 37.9°-38.6° C., NI point 46.2°-46.6° C.

Similarly the following compounds can be prepared:

trans-4-(trans-4-methylcyclohexyl)-1-(2,2-difluoro-1-ethenyl)cyclohexane
trans-4-(trans-4-ethylcyclohexyl)-1-(2,2-difluoro-1-ethenyl)cyclohexane
trans-4-(trans-4-butylcyclohexyl)-1-(2,2-difluoro-1-ethenyl)cyclohexane
CN point 19.9°-20.2° 'C., NI point 45.8°-46.1° C.
trans-4-(trans-4-pentylcyclohexyl)-1-(2,2-difluoro-1-ethenyl)cyclohexane
CS point −1.5° C., SN point 49.2°-49.4° C., NI point 62.1°-62.2° C.
trans-4-(trans-4-hexylcyclohexyl)-1-(2,2-difluoro-1-ethenyl)cyclohexane
trans-4-(trans-4-heptylcyclohexyl)-1-(2,2-difluoro-1-ethenyl)cyclohexane
SN point 49.8°-49.9° C., N-I point 64.7°-64.8° C.
trans-4-(trans-4-octylcyclohexyl)-1-(2,2-difluoro-1-ethenyl)cyclohexane
trans-4-(trans-4-nonylcyclohexyl)-1-(2,2-difluoro-1-ethenyl)cyclohexane
trans-4-(trans-4-decylcyclohexyl)-1-(2,2-difluoro-1-ethenyl)cyclohexane
trans-4-(trans-4-undecylcyclohexyl)-1-(2,2-difluoro-1-ethenyl)cyclohexane
trans-4-(trans-4-dodecylcyclohexyl)-1-(2,2-difluoro-1-ethenyl)cyclohexane
trans-4-(trans-4-methoxycyclohexyl)-1-(2,2-difluoro-1-ethenyl)cyclohexane
trans-4-(trans-4-ethoxycyclohexyl)-1-(2,2-difluoro-1-ethenyl)cyclohexane
trans-4-(trans-4-propoxycyclohexyl)-1-(2,2-difluoro-1-ethenyl)cyclohexane
trans-4-(trans-4-butoxycyclohexyl)-1-(2,2-difluoro-1-ethenyl)cyclohexane
trans-4-(trans-4-pentyloxycyclohexyl)-1-(2,2-difluoro-1-ethenyl)cyclohexane
trans-4-(trans-4-hexyloxycyclohexyl)-1-(2,2-difluoro-1-ethenyl)cyclohexane
trans-4-(trans-4-heptyloxycyclohexyl)-1-(2,2-difluoro-1-ethenyl)cyclohexane
trans-4-(trans-4-octyloxycyclohexyl)-1-(2,2-difluoro-1-ethenyl)cyclohexane
trans-4-(trans-4-nonyloxycyclohexyl)-1-(2,2-difluoro-1-ethenyl)cyclohexane
trans-4-(trans-4-decyloxycyclohexyl)-1-(2,2-difluoro-1-ethenyl)cyclohexane
trans-4-(trans-4-undecyloxycyclohexyl)-1-(2,2-difluoro-1-ethenyl)cyclohexane
trans-4-(trans-4-dodecyloxycyclohexyl)-1-(2,2-difluoro-1-ethenyl)cyclohexane
trans-4-(trans-4-methoxymethylcyclohexyl)-1-(2,2-difluoro-1-ethenyl)cyclohexane

EXAMPLE 7

(i) Preparation of trans-4-(trans-4-propylcyclohexyl)-cyclohexanecarbaldehyde

A mixture of trans-4-(trans-4-propylcyclohexyl)cyclohexanecarbonitrile (100g, 0.43 mol) and toluene (200 ml) was purged by nitrogen gas at 0° C. with stirring, followed by gradually adding a 25 wt. % toluene solution (300 ml) of diisobutylaluminum hydride in nitrogen gas current at a reaction temperature of 5° C. or lower with stirring, gradually raising the reaction temperature up to 20° C. over 3 hours, agitating the resulting material in nitrogen gas current at 20° C. for 10 hours, cooling the reaction mixture down to 0° C., dropwise adding methanol (200 ml) and water (200 ml) and further 6N-hydrochloric acid (500ml) with stirring, adding toluene (300 ml) to the reaction mixture to extract the reaction product, five times washing the toluene solution with a saturated aqueous solution (200 ml) of sodium hydrogen carbonate and further with water till the washing water became neutral, drying the toluene solution over anhydrous sodium sulfate, filtering off the drying agent, distilling off toluene and drying the resulting residue under reduced pressure to obtain the objective product (87 g, 0.37 mol).

(ii) Preparation of trans-4-(trans-4-propylcyclohexyl)-cyclohexylacetaldehyde

Commerically available methoxymethyltriphenylphosphonium chloride (127.5 g, 0.372 mol) was added to methyl t-butyl ether (1 l), followed by adding potassium t-butoxide (43.1 g, 0.384 mol) in argon atmosphere at −10° C. over 10 minutes with stirring, agitating the reaction solution at 0° C. for one hour, dropwise adding a solution of trans-4-(trans-4-propylcyclohexyl)cyclohexanecarbaldehyde (48.9 g, 0.207 mol) obtained in the above item (i) in methyl t-butyl ether (200 ml) at −10° C. over 15 minutes, agitating the reaction mixture at 0° C. for one hour, adding toluene (0.3 l) and water (0.3 l), four times washing the toluene solution with water (0.3 l) in a washing and separating manner, drying the organic layer over anhydrous sodium sulfate, separating the drying agent, distilling off toluene, dissolving the residue in ethyl acetate (100 ml) on heating, allowing the solution to stand still at room temperature for one day, filtering off deposited crystals, concentrating the mother liquor, dissolving the concentrate in heptane and purifying it with to silica gel column chromatography to obtain trans-1-(2-methoxy-1-ethenyl)-4-(trans-4-propylcyclohexyl)cyclohexane (43.1 g, 0.163 mol), adding to the total quantity thereof, tetrahydrofuran (500 ml) and 2N-hydrochloric acid (120 ml), heating the mixture under reflux with stirring for one hour, cooling the reaction mixture, adding toluene (300 ml) and water (1 ml), three times washing the toluene solution with water (1 l) in a washing and separating manner, drying the organic layer over anhydrous sodium sulfate, separating the drying agent, distilling off toluene and drying the residue under reduced pressure to obtain trans-4-(trans-4-propylcyclohexyl)cyclohexylacetaldehyde (38.0 g, 0.152 mol).

(iii) Preparation of trans-1-(3,3-difluoro-2-propenyl)-4-(trans-4-propylcyclohexyl)cyclohexane Trans-4-(trans-4-propylcyclohexyl)cyclohexylacetaldehyde (42.0 g, 0.168 mol) obtained in item (ii), triphenylphosphine (50.6 g, 0.193 mol), sodium chlorodifluoroacetate (51.2 g, 0.336 mol) and dimethylformamide (160 ml) were heated in a nitrogen gas current at about 90° C. for 3 hours with stirring, followed by cooling the reaction mixture down to room temperature, adding toluene (200 ml) and water (200 ml) to the reaction mixture, three times washing the toluene solution with water (200 ml) in a washing and separating manner, drying the organic layer over anhydrous sodium sulfate, separating the drying agent, distilling off toluene, distilling the residue under reduced pressure, dissolving the distillate in heptane, purifying with to silica gel column chromatography, repeating recrystallization from a mixed solvent of heptane and ethanol (1:10) and finally drying the resulting crystals to obtain the objective trans-1-(3,3-difluoro-2-propenyl)-4-(trans-4-propylcyclohexyl)-cyclohexane (18.7 g, 0.0657 mol). This product exhibited a CS point of −11.5° C. and a SI point of 55.4° C.

Similarly the following compounds can be prepared:

4-[trans-4-(3,3-difluoro-2-propenyl)cyclohexyl]-cyclohexane trans-1-(3,3-difluoro-2-propenyl)-4-(trans-4-methylcyclohexyl)cyclohexane trans-1-(3,3-difluoro-2-propenyl)-4-(trans-4-ethylcyclohexyl)cyclohexane trans-1-(3,3-difluoro-2-propenyl)-4-(trans-4-butylcyclohexyl)cyclohexane trans-1-(3,3-difluoro-2-propenyl)-4-(trans-4-pentylcyclohexyl)cyclohexane CS point 3.5° C., SI point 65.7° C.

trans-1-(3,3-difluoro-2-propenyl)-4-(trans-4-hexylcyclohexyl)cyclohexane trans-1-(3,3-difluoro-2-propenyl)-4-(trans-4-heptylcyclohexyl)cyclohexane trans-1-(3,3-difluoro-2-propenyl)-4-(trans-4-octylcyclohexyl)cyclohexane trans-1-(3,3-difluoro-2-propenyl)-4-(trans-4-nonylcyclohexyl)cyclohexane trans-1-(3,3-difluoro-2-propenyl)-4-(trans-4-decylcyclohexyl)cyclohexane trans-1-(3,3-difluoro-2-propenyl)-4-(trans-4-undecylcyclohexyl)cyclohexane trans-1-(3,3-difluoro-2-propenyl)-4-(trans-4-dodecylcyclohexyl)cyclohexane

EXAMPLE 8

Example 7 was repeated except that the starting raw material was replaced by trans-4-propyl(cyanophenyl)-cyclohexane to prepare trans-4-propyl[4-(3,3-difluoro-2-propenyl)phenyl]cyclohexane. This product has a m.p. of −7.0° C.

Similarly the following compounds are prepared:

4-(3,3difluoro-2-propenyl)phenylcyclohexane trans-4-methyl-[4-(3,3-difluoro-2-propenyl)phenyl]-cyclohexane trans-4-ethyl-[4-(3,3-difluoro-2-propenyl)phenyl]-cyclohexane trans-4-butyl-[4-(3,3-difluoro-2-propenyl)phenyl]-cyclohexane trans-4-pentyl-[4-(3,3-difluoro-2-propenyl)phenyl]-cyclohexane trans-4-hexyl-[4-(3,3-difluoro-2-propenyl)phenyl]-cyclohexane trans-4-heptyl-[4-(3,3-difluoro-2-propenyl)phenyl]-cyclohexane trans-4-octyl-[4-(3,3-difluoro-2-propenyl)phenyl]-cyclohexane trans-4-nonyl-[4-(3,3-difluoro-2-propenyl)phenyl]-cyclohexane trans-4-decyl-[4-(3,3-difluoro-2-propenyl)phenyl]-cyclohexane trans-4-undecyl-[4-(3,3-difluoro-2-propenyl)phenyl]-cyclohexane trans-4-dodecyl-[4-(3,3-difluoro-2-propenyl)phenyl]-cyclohexane

EXAMPLE 9

Example 7 was repeated except that the starting raw material was replaced by 4-pentyl-4′-cyanobiphenyl to prepare 4-pentyl-4′-(3,3-difluoro-2-propenyl)biphenyl. This product exhibited SS point of 36.9° C. and SI point of 53.1° C.

Similarly the following compounds are prepared:

4-(3,3-difluoro-2-propenyl)biphenyl
4-methyl-4′-(3,3-difluoro-2-propenyl)biphenyl
4-ethyl-4′-(3,3-difluoro-2-propenyl)biphenyl
4-propyl-4′-(3,3-difluoro-2-propenyl)biphenyl
4-butyl-4′-(3,3-difluoro-2-propenyl)biphenyl
4-hexyl-4′-(3,3-difluoro-2-propenyl)biphenyl
4-heptyl-4′-(3,3-difluoro-2-propenyl)biphenyl
4-octyl-4′-(3,3-difluoro-2-propenyl)biphenyl
4-nonyl-4′-(3,3-difluoro-2-propenyl)biphenyl
4-decyl-4′-(3,3-difluoro-2-propenyl)biphenyl
4-undecyl-4′-(3,3-difluoro-2-propenyl)biphenyl
4-dodecyl-4′-(3,3-difluoro-2-propenyl)biphenyl.

EXAMPLE 10

(i) Preparation of 3-[trans-4-(trans-4-propylcyclohexyl)cyclohexyl]-1propanal

Commerically available methoxymethyltriphenylphosphonium chloride (102.7 g, 0.300 mol) was added to methyl t-butyl ether (1 l), followed by adding potassium t-butoxide (33.7g, 0.300 mol) in argon atmosphere at −10° C. in 10 minutes with stirring, agitating the reaction mixture at 0° C. for one hour, dropwise adding a solution of trans-4-(trans-4-propylcyclohexyl)cyclohexylacetaldehyde (50 g, 0.200 mol) prepared in item (ii) of Example 7, in methyl t-butyl ether (200 ml), at −10° C. in 15 minutes, agitating the reaction mixture at 0° C. for one hour, adding toluene (0.3 l) and water (0.3 l), four times washing the toluene solution with water (0.3 l) in a washing and separating manner, drying the organic layer over anhydrous sodium sulfate, separating the drying agent, distilling off toluene, dissolving the residue in ethyl acetate (100 ml) on heating, allowing the solution to stand still at room temperature for one day, filtering off deposited crystals, concentrating the mother liquor, dissolving the concentrate in heptane and purifying the solution with silica gel column chromatography to obtain trans-1-(3-methoxy-2-propenyl)-4-(trans-4-propylcyclohexyl)cyclohexane (42.6 g, 0.153 mol), adding to the total quantity thereof, tetrahydrofuran (330 ml) and 2N-hydrochloric acid (90 ml), heating the mixture under reflux with stirring for one hour, cooling the reaction mixture, adding toluene (300 ml) and water (1 l), three times washing the toluene solution with water (1 l) in a washing and separating manner, drying the organic layer over anhydrous sodium sulfate, separating the drying agent, distilling off toluene and drying the residue under reduced pressure to obtain 3-[trans-4-propylcyclohexyl)cyclohexyl]-1-propanal (35.6 g, 0.135 mol).

(ii) Preparation of trans-1-(4,4-difluoro-3-butenyl)-4-(trans-4-propylcyclohexyl)cyclohexane 3-[Trans-4-(trans-4-propylcyclohexyl)cyclohexyl]-1-propanal (27.5 g, 0.104 mol) obtained in item (i), triphenylphosphine (31.4 g, 0.120 mol), sodium chlorodifluoroacetate (31.7 g, 0.208 mol) and dimethylformamide (130 ml) were heated in nitrogen gas current, at about 90° C. for 3 hours with stirring, cooling the reaction mixture down to room temperature, adding toluene (200 ml) and water (200 ml) to the solution, three times washing with water (200 ml) in a washing and separating manner, drying the organic layer over anhydrous sodium sulfate, separating the drying agent, distilling off toluene, distilling the residue under reduced pressure, dissolving the distillate in heptane, purifying the solution according to silica gel column chromatography, repeating recrystallization from a mixed solvent of heptane and ethanol (1:10) and finally drying the crystals to obtain the objective compound, trans-1-(4,4-difluoro-3-butenyl)-4-(trans-4-propylcyclohexyl)cyclohexane (10.2 g, 0.0342 mol).

This compound exhibited a CS point of −10.3° C. and an SI point of 70.3° C.

Similarly the following compounds can be prepared using the corresponding aldehyde compounds as raw materials:

4-[trans-4-(4,4-difluoro-3-butenyl)cyclohexyl]-cyclohexane trans-1-(4,4-difluoro-3-butenyl)-4-(trans-4-methylcyclohexyl)cyclohexane trans-1-(4,4-difluoro-3-butenyl)-4-(trans-4-ethylcyclohexyl)cyclohexane trans-1-(4,4-difluoro-3-butenyl)-4-(trans-4-butylcyclohexyl)cyclohexane trans-1-(4,4-difluoro-3-butenyl)-4-(trans-4-pentylcyclohexyl)cyclohexane CS point −22.8° C., SI point 85.7° C.

trans-1-(4,4-difluoro-3-butenyl)-4-(trans-4-hexylcyclohexyl)cyclohexane trans-1-(4,4-difluoro-3-butenyl)-4-(trans-4-heptylcyclohexyl)cyclohexane trans-1-(4,4-difluoro-3-butenyl)-4-(trans-4-octylcyclohexyl)cyclohexane trans-1-(4,4-difluoro-3-butenyl)-4-(trans-4-nonylcyclohexyl)cyclohexane trans-1-(4,4-difluoro-3-butenyl)-4-(trans-4-decylcyclohexyl)cyclohexane trans-1-(4,4-difluoro-3-butenyl)-4-(trans-4-undecylcyclohexyl)cyclohexane trans-1-(4,4-difluoro-3-butenyl)-4-(trans-4-dodecylcyclohexyl)cyclohexane 4-(4,4-difluoro-3-butenyl)phenylcyclohexane trans-4-methyl-[4-(4,4-difluoro-3-butenyl)phenyl]-cyclohexane trans-4-ethyl-[4-(4,4-difluoro-3-butenyl)phenyl]-cyclohexane trans-4-propyl-[4-(4,4-difluoro-3-butenyl)phenyl]-cyclohexane m.p. −15.6° C.

trans-4-butyl-[4-(4,4-difluoro-3-butenyl)phenyl]-cyclohexane trans-4-pentyl-[4-(4,4-difluoro-3-butenyl)phenyl]-cyclohexane trans-4-hexyl-[4-(4,4-difluoro-3-butenyl)phenyl]-cyclohexane trans-4-heptyl-[4-(4,4-difluoro-3-butenyl)phenyl]-cyclohexane trans-4-octyl-[4-(4,4-difluoro-3-butenyl)phenyl]-cyclohexane trans-4-nonyl-[4-(4,4-difluoro-3-butenyl)phenyl]-cyclohexane trans-4-decyl-[4-(4,4-difluoro-3-butenyl)phenyl]-cyclohexane trans-4-undecyl-[4-(4,4-difluoro-3-butenyl)phenyl]-cyclohexane trans-4-dodecyl-[4-(4,4-difluoro-3-butenyl)phenyl]-cyclohexane 4′-(4,4-difluoro-3-butenyl)biphenyl 4-methyl-4′-(4,4-difluoro-3-butenyl)biphenyl 4-ethyl-4′-(4,4-difluoro-3-butenyl)biphenyl 4-propyl-4′-(4,4-difluoro-3-butenyl)biphenyl 4-butyl-4′-(4,4-difluoro-3-butenyl)biphenyl 4-pentyl-4′-(4,4-difluoro-3-butenyl)biphenyl CS point −25.4° C., SS point 30.8° C., SI point 50.6° C.

4-hexyl-4′-(4,4-difluoro-3-butenyl)biphenyl 4-heptyl-4′-(4,4-difluoro-3-butenyl)biphenyl 4-octyl-4′-(4,4-difluoro-3-butenyl)biphenyl 4-nonyl-4′-(4,4-difluoro-3-butenyl)biphenyl 4-decyl-4′-(4,4-difluoro-3-butenyl)biphenyl 4-undecyl-4′-(4,4-difluoro-3-butenyl)biphenyl 4-dodecyl-4′-(4,4-difluoro-3-butenyl)biphenyl

EXAMPLE 11 (USE EXAMPLE 1)

A liquid crystal composition A consisting of

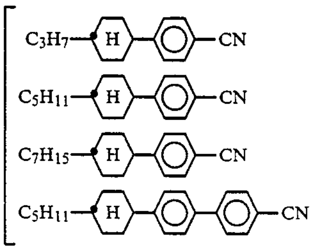

24 parts by weight 36 parts by weight 25 parts by weight 15 parts by weight had a NI point of 72.0° C., a viscosity at 20° C., $\eta_{20}$ of 27.5 cP, a$\Delta\epsilon$ of 11.0 ($\epsilon_{//}$=15.7 and $\epsilon_{\perp}$=4.7) and a $\Delta n$ of 0.14 ($n_e$=1.63 and $n_O$=1.49), and when this composition was placed in a TN cell of 10 μm thick, a threshold voltage was 1.83 V and a saturation voltage was 2.79 V.

When trans-4-propyl-[4-(2,2-difluoro-1-ethenyl)-phenyl]cyclohexane as a compound of the present invention shown in Example 1 (15 parts by weight) was added to the liquid crystal composition A (85 parts by weight), the resulting liquid crystal composition 1 had a NI point of 68.1° C., i.e. not significantly lower, a $\eta_{20}$ of 21.1 cP, i.e., a far reduced $\Delta\epsilon$ of 9.9 ($\epsilon_{//}=14.4$ and $\epsilon_{\perp}=4.5$) and a $\Delta n$ of 0.13 ($n_e=1.62$ and $n_O=1.49$). Further, when this composition was filled in the above mentioned TN cell, a threshold voltage (abbreviated to Vth) was 1.74 V and a saturation voltage (abbreviated to Vsat) was 2.73 V, i.e. both the voltage was reduced.

EXAMPLE 12 (USE EXAMPLES 2-8)

The respective compounds of the present invention prepared in Example 1-6 and shown in Table 1 (15 parts by weight) were added to the above-mentioned liquid crystal composition A (85 parts by weight) to prepare seven liquid crystal compositions. The physical properties of these liquid crystal compositions are shown in Table 1 together with the characteristics of the liquid crystal composition A.

TABLE 1

| Use ex. | Added compound | NI point (°C.) | $\eta_{20}$ (cP) | At 25° C. $\epsilon_{//}$ | $\epsilon_{\perp}$ | $\Delta\epsilon$ | $n_e$ | $n_o$ | $\Delta n$ | $V_{th}$ | $V_{sat}$ |
|---|---|---|---|---|---|---|---|---|---|---|---|
| 2 | 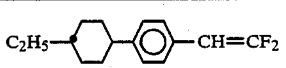 | 63.0 | 20.5 | 14.3 | 4.6 | 9.7 | 1.624 | 1.494 | 0.130 | 1.60 | 2.67 |
| 3 | 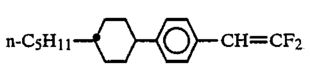 | 68.8 | 22.3 | 14.3 | 4.7 | 9.6 | 1.624 | 1.492 | 0.132 | 1.73 | 2.87 |
| 4 | 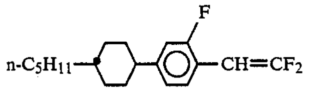 | 65.4 | 21.7 | 14.3 | 4.5 | 9.8 | 1.623 | 1.491 | 0.132 | 1.63 | 2.61 |
| 5 | 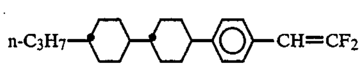 | 91.3 | 27.0 | 13.8 | 4.0 | 9.8 | 1.632 | 1.493 | 0.139 | 2.03 | 3.34 |
| 6 | 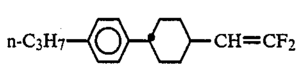 | 52.0 | 21.1 | 14.2 | 4.7 | 9.5 | 1.613 | 1.494 | 0.119 | 1.53 | 2.35 |
| 7 | 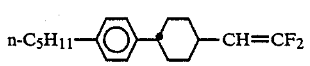 | 50.8 | 23.3 | 14.1 | 4.9 | 9.2 | 1.609 | 1.493 | 0.116 | 1.54 | 2.44 |
| 8 | 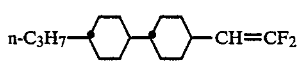 | 68.0 | 20.8 | 13.8 | 4.3 | 9.5 | 1.613 | 1.490 | 0.123 | 1.76 | 2.70 |
| | Liquid composition A | 72.0 | 27.5 | 15.7 | 4.7 | 11.0 | 1.632 | 1.492 | 0.140 | 1.83 | 2.79 |

EXAMPLE 13 (USE EXAMPLE 9)

A liquid crystal composition B consisting of

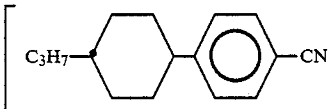
30 parts by weight

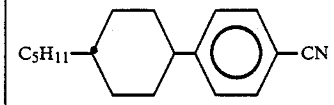
40 parts by weight

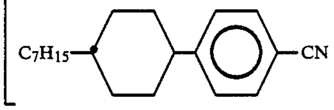
30 parts by weight had a NI point of 52.1° C., a viscosity at 20° C., $\eta_{20}$ of 22.0 cP, a $\Delta\epsilon$ of 10.7 ($\epsilon_{//}=15.9$ and $\epsilon_{\perp}=5.2$) and a $\Delta n$ of 0.119 ($n_e=1.609$ and $n_O=1.490$), and when the composition was placed in a TN cell of 10 μm thick, the threshold voltage Vth was 1.56 V and the saturation voltage Vsat was 2.44 V. Trans-4-(trans-4-propylcyclohexyl)-1-[4-(2,2-difluoro-1-ethenyl)phenyl]-cyclohexane of the present invention shown in Example 3 (15 parts by weight) was mixed with the above-mentioned liquid crystal composition B (85 parts by weight) to prepare a liquid crystal composition 9. This liquid crystal composition 9 had a NI point of 72.4° C., a $\eta_{20}$ of 22.3 cP, a $\Delta\epsilon$ of 9.7 ($\epsilon_{//}=14.0$ and $\Delta_{\perp}=4.3$), a $\Delta n$ of 0.123 ($n_e=1.614$ and $n_O=1.491$), a Vth of 1.80 V and a Vsat of 2.93 V.

EXAMPLE 14 (USE EXAMPLES 10 and 11)

4-Hexyl-4'-(2,2-difluoro-1-ethenyl)biphenyl prepared in Example 5 (15 parts by weight) was added to the liquid crystal composition B used in Example 13 (85 parts by weight) to prepare a liquid crystal composition M, and 4-(trans-4-pentylcyclohexyl)-4'-(2,2-difluoro-1-ethenyl)biphenyl (15 parts by weight) was added to the composition b (85 parts by weight) to prepare a liquid crystal composition N. The values of the physical properties of these liquid crystal compositions were obtained in the same manner as in Example 11. The results are shown in Table 2 together with those of the composition B.

TABLE 2

| Use ex. | | NI point (°C.) | η20 (cP) | At 25° C. ε‖ | ε⊥ | Δε | $n_e$ | $n_o$ | $\Delta_n$ | $V_{th}$ | $V_{sat}$ |
|---|---|---|---|---|---|---|---|---|---|---|---|
| 10 | Composition M | 49.6 | 21.6 | 14.7 | 5.8 | 8.9 | 1.612 | 1.494 | 0.118 | 1.84 | 3.07 |
| 11 | Composition N | 71.5 | 22.8 | 14.4 | 4.5 | 9.9 | 1.628 | 1.492 | 0.136 | 1.72 | 2.82 |
| — | Composition B | 52.1 | 22.0 | 15.9 | 5.2 | 10.7 | 1.609 | 1.490 | 0.119 | 1.56 | 2.44 |

EXAMPLE 15 (USE EXAMPLE 12 )

Trans-1-(4,4-difluoro-3-butenyl)-4-(trans-4-propylcyclohexyl)cyclohexane, a compound of the present invention, shown in EXAMPLE 10 (15 parts by weight), was added to the liquid crystal composition A shown in Example 11 (85 parts by weight). The resulting liquid crystal composition had a NI point of 70.2° C., a $\eta_{20}$ of 1.95 cP, a Δε of 9.5 ($\epsilon_{//}$=13.9 and $\epsilon_{\perp}$=4.4) and a Δn of 0.12 ($n_e$=1.61 and $n_O$=1.49), that is, reduced. Further, when this composition was placed in the above-mentioned TN cell, the threshold voltage (abbreviated to Vth) and the saturated voltage abbreviated to Vsat) lowered down to 1.80 V and 2.77 V, respectively.

EXAMPLE 16 (USE EXAMPLES 13-19)

The respective compounds of the present invention shown in Table 3 (15 parts by weight) were mixed with the above composition A (85 parts by weight) to prepare seven liquid crystal compositions. The physical properties of those seven liquid crystal compositions are shown in Table 3 together with the characteristics of the liquid crystal composition A and the results of the Use example 12.

TABLE 3

| Use ex. | Added compound | NI point (°C.) | η20 (cP) | At 25° C. $\epsilon_{//}$ | $\epsilon_{\perp}$ | Δε | $n_e$ | $n_o$ | Δn | $V_{th}$ (V.) | $V_{sat}$ (V.) |
|---|---|---|---|---|---|---|---|---|---|---|---|
| 12 | 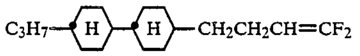 | 70.2 | 19.5 | 13.9 | 4.4 | 9.5 | 1.61 | 1.49 | 0.12 | 1.80 | 2.77 |
| 13 | 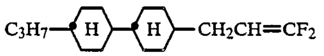 | 61.2 | 20.1 | 14.4 | 4.5 | 9.9 | 1.61 | 1.49 | 0.12 | 1.68 | 2.70 |
| 14 | 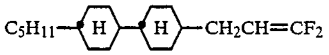 | 63.5 | 20.0 | 13.8 | 4.6 | 9.2 | 1.61 | 1.49 | 0.12 | 1.62 | 2.59 |
| 15 | 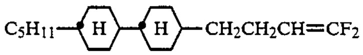 | 71.7 | 21.2 | 13.6 | 4.2 | 9.4 | 1.61 | 1.49 | 0.12 | 1.83 | 2.86 |
| 16 | 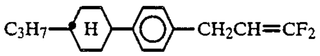 | 48.1 | 21.5 | 14.3 | 5.2 | 9.1 | 1.61 | 1.49 | 0.12 | 1.37 | 2.09 |
| 17 | 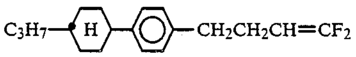 | 57.1 | 20.5 | 13.9 | 4.6 | 9.3 | 1.61 | 1.49 | 0.12 | 1.68 | 2.74 |
| 18 | 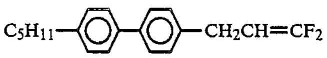 | 52.6 | 21.3 | 14.7 | 4.9 | 9.8 | 1.63 | 1.50 | 0.13 | 1.42 | 2.45 |
| 19 | 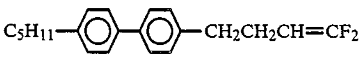 | 59.6 | 21.3 | 14.2 | 4.6 | 9.6 | 1.63 | 1.49 | 0.14 | 1.74 | 2.82 |
| | Liquid crystal composition A | 72.0 | 27.5 | 15.7 | 4.7 | 11.0 | 1.63 | 1.49 | 0.14 | 1.83 | 2.79 |

What we claim is:

1. A compound expressed by the formula $$R^1-A^1-B^1-A^2-(B^2-A^3)_n-(CH_2)_m-CH=CF_2$$

wherein $R^1$ represents a hydrogen atom or an alkyl group or an alkenyl group each of 1 to 20 carbon atoms wherein one $-CH_2-$ group or two $-CH_2-$ groups not adjacent to each other may be substituted by a —O— group; the position and number of said double bond may be optionally chosen; $A^1$, $A^2$ and $A^3$ each independently represent

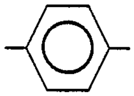

or

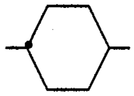

and the hydrogen of this

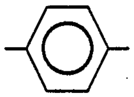

may be substituted by fluorine, chlorine or methyl; $B^1$ And $B^2$ each independently represent —$CH_2CH_2$—, —$CH_2O$—, —$OCH_2$— or a single bond; n represents an integer of 0 or 1; and m represents an integer of 0 to 20.

2. A compound according to claim 1 wherein said n represents 0.

3. A compound according to claim 1 wherein said n represents 0 and said $B^1$ represents a single bond.

4. A compound according to claim 1 wherein said n represents 0 and said $B^1$ represents —$CH_2CH_2$—.

5. A compound according to claim 1 wherein said n represents 0 and said $B^1$ represents —$CH_2O$—.

6. A compound according to claim 1 wherein said n represents 0 and said $B^1$ represents —$OCH_2$—.

7. A compound according to claim 1 wherein said n represents 0, said $B^1$ represents a single bond and said $A^2$ represents

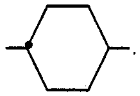

8. A compound according to claim 1 wherein said n represents 0, said $B^1$ represents a single bond and said $A^2$ represents

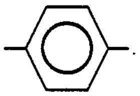

9. A compound according to claim 1 wherein said n represents 1.

10. A compound according to claim 1 wherein said n represents 1 and said $B^1$ and $B^2$ represents a single bond.

11. A compound according to claim 1 wherein said n represents 1 and said $B^1$ and $B^2$ each represent a single bond.

12. A compound according to claim 1 wherein said n represents 1, said $B^1$ and $B^2$ each represent a single bond and said $A^2$ represents

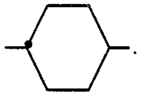

13. A compound according to claim 1 wherein said n represents 1, said $B^1$ and $B^2$ each represent a single bond and said $A^2$ represents

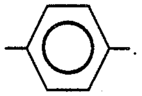

14. A compound according to claim 1 wherein said n represents 1, said $B^1$ represents —$CH_2CH_2$— and said $B^2$ represents a single bond.

15. A liquid crystal composition comprising at least two components at least one of which is a compound as set forth in claim 1.

16. A liquid crystal composition according to claim 15 wherein the content of a compound as set fourth in claim 1 is 1 to 30% by weight based on the weight of said liquid crystal composition.

* * * * *